United States Patent [19]

Grassin et al.

[11] Patent Number: 5,639,494
[45] Date of Patent: Jun. 17, 1997

[54] PECTINESTERASE IN THE TREATMENT OF FRUIT AND VEGETABLES

[75] Inventors: Catherine Marie Therese Grassin; Pierre Clement Louis Fauquembergue, both of Seclin, France

[73] Assignee: Gist-brocades, N.V., Ma Delft, Netherlands

[21] Appl. No.: 256,856

[22] PCT Filed: Nov. 30, 1993

[86] PCT No.: PCT/EP93/03379

§ 371 Date: Dec. 5, 1994

§ 102(e) Date: Dec. 5, 1994

[87] PCT Pub. No.: WO94/12055

PCT Pub. Date: Jun. 9, 1994

[30] Foreign Application Priority Data

Nov. 30, 1992 [EP] European Pat. Off. ............. 92203689

[51] Int. Cl.⁶ ........................................................ A23L 1/05
[52] U.S. Cl. ..................... 426/50; 426/49; 426/52; 426/573; 426/577; 426/615
[58] Field of Search ........................ 426/50, 49, 52, 426/615, 616, 573, 574, 577

[56] References Cited

U.S. PATENT DOCUMENTS

| 2,754,214 | 7/1956 | Leo et al. ............................ 426/50 |
| 3,615,721 | 10/1971 | Silberman ........................... 426/50 |
| 3,917,867 | 11/1975 | Atkins et al. ....................... 426/492 |
| 4,109,017 | 8/1978 | Grampp et al. ...................... 426/51 |
| 4,200,694 | 4/1980 | Ishii et al. ........................ 426/50 |

FOREIGN PATENT DOCUMENTS

| 84317 | 9/1971 | German Dem. Rep. ........... 426/50 |
| 0025673 | 2/1984 | Japan .............................. 426/50 |
| 9005463 | 5/1990 | WIPO ............................... 426/50 |
| 9100022 | 1/1991 | WIPO ............................... 426/50 |

OTHER PUBLICATIONS

Bock et al., Derwest Abstract 84–024248, PD202620, Sep. 1983.
Pilnik et al., "The Biochemistry of Fruits and their Products", Academic Press (Hulme), vol. 1, 53–87 (1970).

*Primary Examiner*—Leslie Wong
*Attorney, Agent, or Firm*—Morrison & Foerster LLP

[57] ABSTRACT

A method to prepare a food containing a gel of a low-methoxylated pectin of at least one fruit or vegetable is disclosed. The method comprises adding pectin esterase to the fruit or vegetable or to the pulp thereof in an amount effective to demethoxylate pectin, optionally adding calcium chloride, and maintaining the fruit or vegetable or pulp under conditions such that the pectin esterase converts high-methoxylated pectin of the fruit or vegetable or pulp to low-methoxylated pectin and the low-methoxylated pectin forms a gel. The fruit or vegetable or pulp is then formulated to obtain the desired food containing the gel. The method is used, for instance, to produce fruit and vegetable jams and jellies, compotes, sauces and soups.

18 Claims, 1 Drawing Sheet

PECTINESTERASE IN THE TREATMENT OF FRUIT AND VEGETABLES

TECHNICAL FIELD

The present invention relates to the use of pectinesterase (E. C. 3.1.1.11) in the preparation of food containing fruits or vegetables. Specifically, the invention relates to the use of pectinesterase in the treatment of fruit or vegetables that is in the demethoxylation of pectin. The treated fruits or vegetables are then used in the preparation of jams, jellies, compotes, sauces and soups. The present invention further discloses a modification to the standard US apple sauce preparation process.

BACKGROUND OF THE INVENTION

Fruit and vegetable jams and jellies are normally prepared by cooking protreated fruit and subsequent cooling. The pectin present in the fruit gelates, thereby giving the jam or jelly its rheological characteristics. The pectin is mainly responsible for this gel formation due to its gelifying power. The gelifying potential of pectin is dependent on several conditions, mainly:

dry substance content or brix, pH of the fruit or vegetable, concentration of pectin normally present, degree of methylation of the pectin.

Pectins are major constituents of the cell walls of edible parts of fruits and vegetables. The middle lamella which are situated between the cell walls are mainly build up from protopectin which is the insoluble form of pectin. Pectins are considered as intercellular adhesives and due to their colloid nature they also have an important function in the water-regulation of plants. Waterbinding capacity is greatly increased by the amount of hydrophylic hydroxyl and carboxyl groups. The amount of pectin can be very high. For example, lemon peels are reported to contain pectin upto 30% of their dry weight, orange peels contain from 15–20% and apple peels about 10% (Norz, K., 1985. Zucker und S$\bar{u}$sswaren Wirtschaft 38 5–6).

From a chemical point of view pectin consist of methoxylated polygalacturonic acid residues. Pectins are classified in differemt categories based on the degree of esterification and the degree of polymerisation.

On the basis of the degree of esterification pectins are divided into two groups:

1) high-methoxylated pectins with a degree of esterification higher than 50%, and 2) low-methoxylated pectins having a degree of esterification lower than 50%.

Both of these groups are capable of forming gels, however these gels differ in the mechanism by which they are formed. The high-methoxylated pectins form gels based on dehydration and electrical neutralisation of colloidal pectin-agglomerates. Gelation is stimulated if the pH is about 3 (dependent on the fruit or vegetable in question) and sugar, needed for the dewatering, is present in more than 60% dry weight. Depending on the fruit, in practice, this often means that both sugar and high-methoxylated pectin have to be added to obtain the classical high sugar content jams. Structure forming interactions in the high-methoxylated pectin containing gels is based on hydrogen bond formation.

The low-methoxylated pectins are capable of forming gels with calcium ions or other divalent cations only. Gel formation with low-methoxylated pectins is based on ionic interactions. Calcium ions are naturally present in for example apples. No sugars have to be added in order to obtain suitable gelling properties. The amount of sugar and the pH in this case only influence the speed and temperature of gelifying. Low-methoxylated pectins are therefore perfectly suited for the preparation of low sugar content jams and jellies.

In practice pectin from fruits and vegetables generally has a high degree of methoxylation which necessitates the addition of large amounts of sugars to obtain suitable rheological characteristics. Furthermore, the degree of methoxylation varies with the time elapsed between the harvesting and the processing of the vegetables or fruit. This leads to a difference in the viscosity of the produced jams and jellies if the processing conditions are kept constant.

SUMMARY OF THE INVENTION

The present invention discloses the use of pectinesterase in the preparation of food containing fruits or vegetables. Specifically, the invention discloses the use of pectinesterase in the treatment of fruit or vegetables that is in the demethoxylation of pectin. The treated fruits or vegetables are then used in the preparation of jams, jellies, compotes, sauces and soups.

The pectinesterase is used to demethoxylate the high-methoxylated pectins to obtain low-methoxylated pectins. The pectins obtained in this manner show calcium dependent gelation. This gel formation does not require the addition of sugars.

The present invention discloses jams and jellies obtained after the use of pectinesterase.

Furthermore, the present invention discloses a method for treating the crude fruit products with pectinesterase.

The present invention also discloses a process for obtaining apple sauce comprising the use of pectinesterase. Furthermore, the present invention discloses how the characteristics of the apple sauce are improved using pectinesterase in the standard US apple sauce preparation process. The invention also discloses how this standard process can be improved by a slight alteration in the process i.e. the introduction of a holding tank at a certain process stage.

DESCRIPTION OF THE INVENTION

Figure 1:
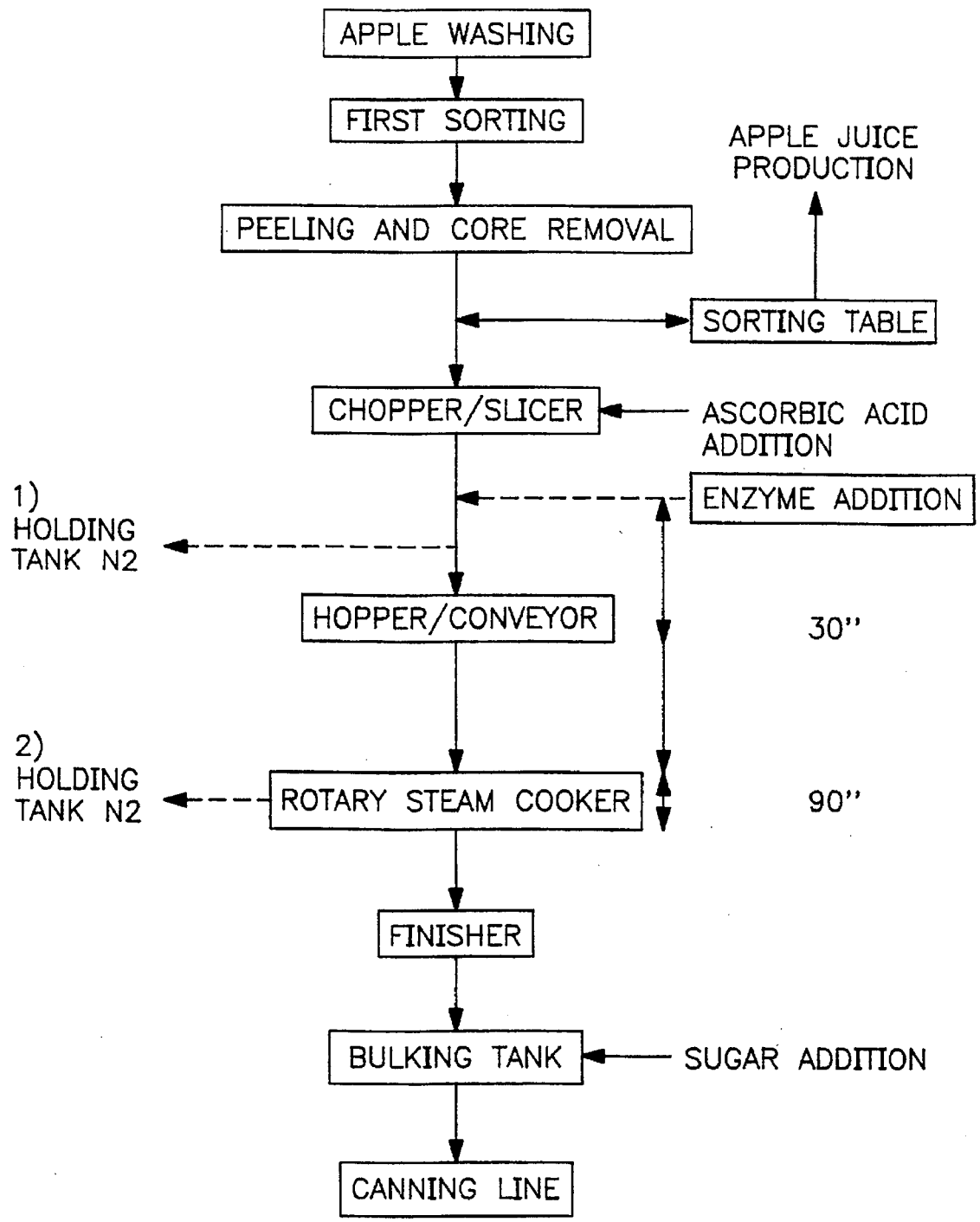
FIG. 1 is a schematic presentation of the apple sauce preparation process as used in the USA. The holding tanks 1) and 2) are suggested modifications to the standard process.

The present invention discloses the use of pectinesterase in the preparation of food containing fruit or vegetables. The present invention discloses a method for preparing food containing fruit or vegetables comprising the addition of pectinesterase to the fruit or vegetable or to the pulp thereof to demethoxylate the pectin, and optionally, the addition of calciumchloride allowing the mixture to form a gel and further formulating the so-treated fruit or vegetable to obtain the desired food.

Preferably, the fruit or vegetable is selected from the group of fruits or vegetables containing high-methoxylated pectins.

Specifically, the invention is used in the preparation of fruit and vegetable jams and jellies, compotes, sauces and soups.

The inventors demonstrate that it is possible to treat crude fruit or vegetable products with pectinesterase, that due to this treatment the degree of methoxylation of the pectin is lowered and that the resulting pectin gelifies with the calcium that is present in the fruit or vegetable. If the gelling is not complete it is possible to add high methoxylated pectin before enzyme addition or to add low-methoxylated pectin.

This process works well with fruits or vegetables which contain high-methoxylated pectins, such as apple, strawberry, blackcurrant, orange, peach, pear, apricots and raspberry.

In the present invention both-strawberries and apples were used. The first since it is a popular jam species and the second for its high content of high-methoxylated pectins.

Pectinesterases suitable for performing this process can be obtained from different sources. The pectinesterase of the present invention can be any pectiaesterase from plants, bacteria or fungi, suitable for the degradation of high-methoxylated pectin. Preferably, the pectinesterase is from fungal origin. More preferably, the pectinesterase is obtained from Aspergilli, especially preferred is the use of pectinesterase obtained from *Aspergillus niger*.

In a most preferred embodiment purified pectinesterase is used. This purification can be performed in different ways.

The crude enzyme may be purified for example by liquid chromatography (ion exchange, gel filtration, affinity) (Ishii et el., *1980*. Deutsches Patentamt Auslegeschrift 2843351) or by selective inhibition of the pectin depolymerases (pH shock, heat shock, chemical inhibitors, chemical or organic solvents extraction) (Smythe C. et el., 1952. U.S. Pat. No. 2,599,531) Another source for obtaining purified pectinesterase as defined for the present application is pectinesterase obtained by recombinant DNA technology. An example of the use of recombinant DNA technology is the expression cloning of the *Aspergillus niger* pectinesterase. The cDNA sequence of this gene has been reported (Khanh et el. Nucl. Acids Res. 18 4262 (1990)). As expression host *Aspergillus niger* could be used. However, in view of the possible contamination of the pectinesterase with polygalacturonase, pectin lyase and other pectin depolymerases it may be preferable to use a heterologous host organism for producing the pectinesterase.

Suitable host organisms include bacteria and fungi. Preferred species are Bacilli, Escherichia, Saccharomyces, Kluyveromyces and Aspergilli.

The pectinesterase treatment of the present invention can be performed on entire fruits or vegetables, it can also be performed on presliced or ground fruits or vegetables. The pectinesterase treatment of fruit or vegetables is performed as follows;

pectinesterase is added to the crude or pretreated fruit or vegetable, the amount may vary as long a clear effect on the viscosity of the final product is detectable. Effective amounts, as shown for example in Examples of the present invention range from about 30–500 PE units per kg. These values merely serve as indications. It is understood that the effect of pectinesterase does not only depend on the amount of enzyme added but also on the time the enzyme performs its activity.

also required for obtaining the desired gels is the addition of cations. In the present description this is illustrated by the use of calciumchloride. Again calcium ions are to added in effective amounts. In Example 1 this is 250 ppm in the form of calciumchloride.

the temperature of the reaction is not critical and may range from 10°–70° C.

reaction time again is not critical. Under application conditions it is desirable to keep reaction times low, for economical reasons. It is shown that a reaction time of about 10 minutes leads to a considerable improvement in the quality of apple sauce.

finally the reaction is stopped by heat inactivation of the enzyme. This inactivation may coincide with the sterilisation of the product before canning or packaging.

The treatment leads to an increased firmness and viscosity of the product. After enzymatic treatment the fruits or vegetables can be added to dairy, bakery or confectionary products such as yoghurts, ice creams or desserts. The products can also be used as jams or jellies or fillings for chocolates, cakes or sweets. Another use is in the coating of other food products. By treating entire fruits or vegetables prior to freezing the firmness of the fruits or vegetables after defreezing is increased. The pectinesterase treatment can also be used to improve the firmness of the entire fruits or vegetables. Pectinesterase treatment before blanching or cooking can be used to retard or prevent softening of the fruit or vegetable.

Retarding vegetable softening by cold alkaline pectin deesterification before cooking has been reported (van Buren and Pitifer. J.Food Sci. 57 1022–1023 (1992)) and it is to be expected that enzymatic deesterification also retards the indicated softening.

Apart from the direct uses of the treated fruit or vegetables as mentioned above, the application of the low-methoxylated pectins diminishes or abolishes the required use of sugars or other gelifying agents. After treatment of high-methoxylated pectin containing fruits or vegetables with pectinesterase the use of texturing agents such as exogenous pectin or of gelling or thickening agents obtainable from higher plants, seaweeds, animals or microorganisms (such as alginate or carageenan) can be largely diminished.

A further advantage of the use of gels from low-methoxylated pectins is that in comparison with high-methoxylated pectin gels the gels are irreversible. This means that heating and subsequent cooling does not destroy the gel. This heating and cooling is responsible for the well-known increase in fluidity of the jams upon storage. To the expert in is clear from the above that pectinesterase may be used in any foodstuff where low-methoxylated pectins normally are applied. Examples of such foodstuffs are apart form the mentioned jams and jellies all kinds of fruit fillings, glazes and aspics. Instead of using low-methoxylated pectin as such the low-methoxylated pectin can be obtained by in situ formation from high-methoxylated pectins through the action of pectinesterase. In principle the formation of the (partially) demethylated pectin can be performed during any phase of the manufacturing process.

The present invention is illustrated by treatment of apples and strawberries with pectinesterase and it is shown that the viscosity is considerably increased after using the demethoxylating enzyme this effect is even more pronounced upon the addition of calciumchloride. The gelfirmness, measuresed as grams of counterpressure using a Stevens Texture Analyser, increases upon treatment with pectinesterase. By adding calciumchloride the firmness can even be increased more.

In other examples it is shown that under normal processing conditions the viscosity of apple sauce is increased following treatment with pectinesterase.

Use of pectinesterase leads to a better consistency as measured by the flow ring method. Consistency is an important measure for the quality of apple sauce. Other improvements related to the use of pectinesterase in apple sauce preparation process are, a better mouthfeel and the absence of free run juice.

The results of the industrial trials indicate that pectinesterase can be used with its profitable effect without any alterations to the present production process.

The incorporation of pectinesterase in the present US standard apple sauce production process, without altering the process as such, leads to a very short reaction time for the pectinesterase (80–120 seconds). Even with this short reaction time pectinesterase gives clearly favorable effects on the product quality. This prompted the inventors to study the effect of a longer reaction time of the pectinesterase on the quality of the apple sauce. Bench-scale experiments indicated that increase of the reaction time to about 10 minutes increases the product quality even more.

Therefore, as another aspect the present invention discloses an altered production process for the preparation of apple sauce. The alteration consists of the introduction of a holding tank in the apple sauce preparation process in order to increase the effective reaction time of pectinesterase. It is suggested to keep the holding tanks under nitrogen and ad room temperature if positioned at position 1) at position 2) the temperature is preferably about 60° C. The prefered holding time is about 10 minutes and the volume of the tank should be chosen accordingly. The present invention therefore discloses a process for preparing apple sauce whrein the following steps are performed;

1) washing of apples, 2) sorting to remove bad apples, 3) peeling and removal of the core, 4) sorting to remove bad apples, 5) crushing, chopping or slicing of the apples, 6) hopping of the apples to the cooker, 7) steam cooking of the apples, 8) finishing i.e. removing of stamens, peels, seed and other undesired particles, 9) addition of sugar, 10) canning, characterized in that pectinesterase is added to the apples after crushing, chopping of slicing of the apples.

In an improved version of this process a holding tank is addded after the enzyme addition step and before the steam cooking step. The holding tanks are preferably kept under nitrogen and the holding time, which varies with the temperature, the amount of enzyme added and the desired apple sauce consistancy.

The use of pectinesterase in the apple sauce process allows for the product/on of top (constant) quality apple sauce during the whole season. As mentioned before the degree of methoxylating changes with the time after harvesting. The quality of the apple sauce using a standard process thus depends on the freshness of the fruits used in the process. Enzymatic demethoxylation leads to a constant and reproducible degree of methoxylation and thus to a constant quality gel or apple sauce.

EXAMPLES

Experimental

Assay of pectin esterase activity

One PE unit as used in the present specification is defined as the amount of enzyme which hydrolizes one microequivalent carboxymethyl in one minute under reaction conditions at 30° C. and pH=4.5. The substrate is Apple pectin Ruban Brun 0.5% with a methylation degree of over 70% in water.

One PE Unit=0.98 PE International Unit. Experiments are performed with pectinesterase which is preferably free from pectin lyase and polygalacturonase activities. Purification can be performed by standard methods as mentioned in the description.

EXAMPLE 1

Pectinesterase treatment of fruit and influence on firmness

In the present experiments strawberries and apples were used.

Strawberries, without the green pans, were ground using a Waring blender for 30 seconds at low speed.

Apples; a blend of 33% Golden Delicious, 33% Red Delicious and 33% Granny Smith were first cut into small pieces, without the stem. Subsequently the apples were strained with the aid of a Roto shredder fixed on a Hobart mixer (model N-50G, speed 2). The mass was then grinded, for 30 seconds (high speed), using a Waring blender (model 32BLB0).

The fruit pulp (strawberries and apples were treated in the same manner) was devided into six portions of 300 grams and each portion was poured into an erlenmeyer flask.

Pectinesterase (240 PE units/g) was added to the pulp in two different concentrations. As can be seen in Table 1, flasks 1 and 2 were blanks. Flasks 3 and 4 contained 250 PE units/kg and flasks 5 and 6 contained 500 PE units/kg.

The flasks were placed in a waterbath (50° C.) and stirred using a magnetic stirrer. After one hour, calciumchloride was added to flasks 2, 4 and 6 and enzyme activity was stopped by placing all erlenmeyers in a boiling waterbath for 2.5 min.

Finally, the hot pulp was poured into plastic cups (300 ml) and left to stand for 24 hours at room temperature.

Firmness of the jellies was measured with the aid of a Stevens Texture Analyser. Thereto a cylindrical plunger (TA4 1,5 inch) is brought into the gel at a constant speed (0.5 mm/s). Firmness is defined as the force required (in g) to penetrate the gel for a specified depth (5 mm). Duplicate measurements were performed. Results are shown in Table 1.

TABLE 1

| Gelfirmness in grams counterpressure for penetration of 5 mm. | | |
|---|---|---|
| Flask | Strawberry | Apple |
| 1 Blank pulp | 13 | 45 |
| 2 Blank pulp + 250 ppm CaCl$_2$ | 13 | 45 |
| 3 Pulp + 250 PE u/kg | 73 | 121 |
| 4 Pulp + 250 PE u/kg + 250 ppm CaCl$_2$ | 56 | 250 |
| 5 Pulp + 500 PE u/kg | 126 | 144 |
| 6 Pulp + 500 PE u/kg + 250 ppm CaCl$_2$ | 117 | 249 |

The low firmness of flasks 1 and 2 indicates that gelification has occurred.

Flask 3 shows that gelification takes place in both apple and strawberries after addition of pectinesterase. Higher PE concentrations lead to increased firmness (flask 5).

The influence of calcium on gelification clearly depends on the type of fruit. The relatively low calcium concentration of apples, apparently inhibits a quick gelification of the high concentration of demethylated pectin. Addition of calcium then increases the gel strength and the rate of gelification.

In strawberries the calcium concentration is relatively high, in combination with a low pectin concentration the addition of calcium results in a non-optimal calcium pectin ratio. This leads to a lower gel strength.

EXAMPLE 2

Influence of pectinesterase treatment on viscosity of apple sauce under large-scale processing conditions In a typical large scale (3–5 tons) process the apples (Golden delicious) are washed and ground. The temperature of this pulp is brought to 90° C. by addition of fresh pulp to pulp kept at 94° C. in a ratio of 1:9 (the so-called Hot-break process). The pulp is kept at 90° C. for 10 to 15 min before further processing.

Rapidase™ 9236 was added during the grinding at 150 g/ton and at 300 g/ton. Viscosity was measured by taking samples at different times and cooling these samples to a standard temperature. Subsequently, these samples were applied on a plate having a fixed inclination and the distance travelled by the front of the pulp was measured after 1 or 2 minutes. The distance is a measure for the viscosity of the sample.

Results are shown in Table 2.

TABLE 2

| Dose Rapidase 9236 Temp. of measurement | 150 g/ton | | | 300 g/ton | |
|---|---|---|---|---|---|
| | 33° C. | 21° C. | | 21° C. | |
| | distance (mm) measured after | | | | |
| | 1 min. | 1 min. | 2 min. | 1 min. | 2 min. |
| Time of measurement after start of PE addition | | | | | |
| 0 | 40 | 34 | 38 | 29 | 32 |
| 20 | 35 | 30 | 34 | 30 | 31 |
| 25 | 30 | 27 | 30 | 25 | 28 |
| 30 | 30 | 26 | 29 | 27 | 29 |
| 35 | 30 | 25 | 30 | 28 | 30 |
| 40 | 31 | 26 | 30 | 29 | 31 |
| 45 | 33 | 27 | 31 | 30 | 31 |
| 55 | 34 | 30 | 34 | 28 | 30 |

It can be calculated that the pulp was fully mixed with enzyme between 25 and 40 minutes. After and before these times the pulp was increasing respectively, decreasing in amount of pectinesterase.

It can be concluded that viscosity increases due to pectinesterase treatment under processing conditions. With 300 g/ton the increase in viscosity was less then expected probably due to an overdosage of pectinesterase with a concurrent lack of a sufficient amount of calcium.

EXAMPLE 3

Use of pectinesterase in an industrial process for production of apple sauce

Enzyme preparation

In the present example pectinesterase from Aspergillus was used the enzyme had an activity of 260 PE units/g.

Viscosity measurement

Viscosity measurement was performed using the flow ring (via flow) as recommended by the USDA (United Sates Department of Agriculture).

Free run juice measurement

Free run juice was estimated visually. Quantities are indicated as follows:

+++a lot of free run juice

++medium amount of free run juice

+small amount of free run juice

−no free run juice

Mouthfeel test

The mouthfeel is graded by tasting. The following gradations are given:

poor taste medium taste good taste very good taste

Description of the industrial apple sauce preparation process

Industrial apple sauce preparation is performed by the following processing steps. The process described is the one normally used in the USA. This process differs from the one used in Europe. The process is schematically presented in FIG. 1.

Description of the process for apple sauce preparation in the USA

The process for apple sauce preparation comprises the following steps:

1) washing of apples 2) 1st sorting to remove bad apples 3) peeling and removal of the core 4) 2nd sorting to remove bad apples 5) crushing )

chopping ) different types of crushers slicing )

6) hopper conveyor—conveyor to cooker 7) steam cooker—pulp heating to 93°–94° C.

8) finisher—removing of stamens, peels, seed and other undesired particles 9) bulking tank for sugar addition 10) canning line Experiments Three trials were performed at industrial scale. Pectinesterase was added during transport of the sliced apples on the conveyor to the cooker. Effective reaction time for the pectinesterase was therefore very short, 80–120 seconds. The temperature during the reaction on the conveyor was 60° C. As mentioned before the mixture was heated by mixing with a mixture of 93°–94° C. in a ratio of 1:9.

I. Contact time enzyme (max): 80 seconds.

Medium quality of apples, chopper: coarse paticles.

Enzyme 1200 g/ton apples.

Temperature 60° C. at the place of addition.

| | Average consistancy | Free run juice | Mouthfeel |
|---|---|---|---|
| No enzyme (before test) | 6.37 | ++ | ND |
| With enzyme | 6.01 | + | ND |
| No enzyme (end of trial) | 7.04 | +++ | ND |

II. Contact time enzyme (max): 120 seconds.

Good quality of apples, chopper: small paticles.

Enzyme 1000 g/ton apples.

Temperature 60° C. at the place of addition.

|  | Average consistancy | Free run juice | Mouthfeel |
|---|---|---|---|
| No enzyme (before test) | 5.9 | – | good |
| With enzyme | 5.4 | – | very good |
| No enzyme (end of trial) | 5.9 | – | good |

III. Contact time enzyme (max): 120 seconds.
Good quality of apples, chopper: small paticles.
Enzyme 600 g/ton apples.
Temperature 60° C. at the place of addition.

|  | Average consistancy | Free run juice | Mouthfeel |
|---|---|---|---|
| No enzyme (before test) | 6.26 | ++ | good |
| With enzyme | 5.75 | – | very good |
| No enzyme (end of trial) | 6.32 | ++ | good |

It can be seen that through the addition of pectinesterase, without any alterations to the apple sauce production process, the taste of the apple sauce can be improved.

The criterium of consistancy is the most important for grading different apple sauce preparations, it is related directly to the level and quality of pectine in the apple. The industrial trials show an improvement of the consistancy of the apple sauce after the use of pectinesterase.

In addition to the increase in consistancy an improvement of mouthfeel was observed. Furthermore, the absence of free run juice is another sign of increased quality of the apple sauce upon usage of pectinesterase.

The difference between the starting values is due to the fact that the measurements have been performed at three different production facilities, the apples were not the same brand and possibly from a different season.

EXAMPLE 4

Effect of pectinesterase on consistancy at different dosage

One gallon can of apple sauce was recovered from the canning line (Example 3, second trial) before cooling and at a temperature of 65°–70° C.

Four trials have been performed on 500 gram samples of apple sauce. The trials consisted in the addition of different amounts of pectinesterase. The mixtures were kept at 60° C. for 10 minutes, subsequently the temperature was raised to 92° C. in a microwave oven. The consistancy and the amount of free run juice were measured as described in Example 3.

| Trial | dosage | consistancy | free run juice |
|---|---|---|---|
| 1 | control | 5.70 | + |
| 2 | 200 g/ton | 5.0 | – |
| 3 | 400 g/ton | 4.85 | – |
| 4 | 600 g/ton | 4.50 | – |

The results indicate that the quality of the apple sauce is further improved, as evidenced by the consistancy and the amount of free run juice, by increasing the reaction time and concentration of the pectinesterase.

Values below 5.5 can easily be reached and this value is considered to be of importance in pricing of the product.

EXAMPLE 5

Effect of oectinesterase on consistancy at different temperatures

The apple sauce was recovered from the canning line as described in the previous example. The apple sauce (500 gram samples) was heated to the indicated temperatures and pectinesterase was added in an amount of 400 g/ton. The samples were left to cool. Consistancy, free run juice and mouthfeel were determined as described in Example 3.

| Trial | temperature | consistancy | free run juice | mouthfeel |
|---|---|---|---|---|
| 1 | control | 5.70 | + | good |
| 2 | 82° C. | 5.45 | – | good |
| 3 | 75° C. | 5.30 | – | very good |
| 4 | 70° C. | 5.0 | – | very good |
| 5 | 65° C. | gel | – | – |
| 6 | 60° C. | gel | – | – |

The results indicate that the consistancy, free run juice and mouthfeel improve upon using pectinesterase. This effect is temperature dependent as can be expected for enzyme activities.

We claim:

1. A method to prepare a food containing a gel of low-methoxylated pectin of at least one fruit or vegetable which method comprises:
   adding pectin esterase to the fruit or vegetable or to the pulp thereof in an amount effective to demethoxylate pectin;
   maintaining said fruit or vegetable or pulp under conditions such that said pectin esterase converts high-methoxylated pectin of said fruit or vegetable or pulp to low-methoxylated pectin and said low-methoxylated pectin forms a gel; and
   formulating the fruit or vegetable or pulp to obtain the desired food comprising said gel.

2. The method of claim 1 wherein said fruit or vegetable contains high-methoxylated pectin.

3. The method of claim 1 wherein the fruit is apple, strawberry, orange, peach, pear, apricots, raspberry or blackcurrant.

4. The method of claim 1 which is conducted in the absence of additional gelling or thickening agents.

5. The method of claim 1 wherein the pectin esterase is of fungal origin.

6. The method of claim 5 wherein the fungus is Aspergillus.

7. The method of claim 1 wherein the pectin esterase is added in purified form.

8. The method of claim 1 further comprising the step of adding calcium chloride prior to allowing said low methoxylated pectin to form a gel.

9. The method of claim 1 wherein said food is selected from the group consisting of jams, jellies, compotes, sauces and soups.

10. A process for converting a fruit or vegetable or pulp thereof containing high-methoxylated pectin into a food product having increased viscosity which process comprises:
   adding pectin esterase to a liquid-containing composition comprising the fruit or vegetable or pulp thereof in an amount effective to demethoxylate high-methoxylated pectin;
   maintaining said liquid-containing composition under conditions such that said pectin esterase converts at least some of said high-methoxylated pectin to pectin with a lower degree of methoxylation and said pectin with a lower degree of methoxylation increases the viscosity of said liquid-containing composition; and formulating said liquid-containing composition to obtain the desired food product having increased viscosity, which food product comprises said fruit or vegetable or pulp thereof and said pectin with a lower degree of methoxylation.

11. A process according to claim 10 wherein the fruit is apple, strawberry, blackcurrent, orange, peach, pear, apricots or raspberry.

12. A process according to claim 10 wherein said pectin esterase is added in an amount of between 50 and 500 PE units per kilogram of fruit or vegetable or pulp.

13. A process according to claim 10 wherein said food product is selected from the group consisting of jams, jellies, compotes, sauces and soups.

14. A process according to claim 10 wherein said food product is a filling for a chocolate, cake or sweet.

15. A process according to claim 10 wherein after adding said pectin esterase said liquid-containing composition is maintained under conditions such that said pectin esterase converts high methoxylated pectin to pectin with a lower degree of methoxylation for not more than about ten minutes.

16. The process according to claim 10 wherein said pectin esterase is obtainable from a fungus which is a species of Aspergillus.

17. A process according to claim 10 for converting apples to applesauce having increased viscosity, which process comprises (a) adding to a liquid-containing composition consisting essentially of prepared apples an amount of pectin esterase effective to lower the degree of methoxylation of pectin contained in said apples wherein the apples have been prepared by peeling and removal of the core, removing bad apples, and crushing, chopping or slicing the remaining apples;

(b) maintaining said composition under conditions sufficient for the demethoxylation activity of said pectin esterase to produce an increase in the viscosity of said composition; and (c) steam cooking the apples treated as set forth in (a) and finishing in a process which comprises removing undesired particles, adding sugar and canning.

18. The method of claim 17 comprising the additional step of placing the treated apples of step (a) in a holding tank prior to the steam cooking step of step (c).

* * * * *